US012770742B2

(12) United States Patent
Wang et al.

(10) Patent No.: US 12,770,742 B2
(45) Date of Patent: Oct. 20, 2026

(54) DETERMINING ERRONEOUS CODES IN MEDICAL REPORTS

(71) Applicant: KONINKLIJKE PHILIPS N.V., Eindhoven (NL)

(72) Inventors: Xin Wang, Cambridge, MA (US); Yugang Jia, Winchester, MA (US); Merlijn Sevenster, Haarlem (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1468 days.

(21) Appl. No.: 16/980,141

(22) PCT Filed: Mar. 14, 2019

(86) PCT No.: PCT/EP2019/056408

§ 371 (c)(1),
(2) Date: Sep. 11, 2020

(87) PCT Pub. No.: WO2019/175302

PCT Pub. Date: Sep. 19, 2019

(65) Prior Publication Data

US 2021/0012066 A1 Jan. 14, 2021

Related U.S. Application Data

(60) Provisional application No. 62/642,958, filed on Mar. 14, 2018.

(51) Int. Cl.

| | |
|---|---|
| ***G16H 50/70*** | (2018.01) |
| ***G06F 16/23*** | (2019.01) |
| ***G06N 20/00*** | (2019.01) |
| ***G16H 70/20*** | (2018.01) |

(52) U.S. Cl.

CPC ......... *G16H 50/70* (2018.01); *G06F 16/2379* (2019.01); *G06N 20/00* (2019.01); *G16H 70/20* (2018.01)

(58) Field of Classification Search

None

See application file for complete search history.

(56) References Cited

U.S. PATENT DOCUMENTS

| | | | | |
|---|---|---|---|---|
| 11,024,424 | B2 * | 6/2021 | Sun | G16H 10/60 |
| 2008/0004505 | A1 | 1/2008 | Kapit | |
| 2011/0188706 | A1 | 8/2011 | Zhou | |
| 2014/0149407 | A1 | 5/2014 | Qian | |
| 2017/0024656 | A1 | 1/2017 | Gilon | |
| 2017/0199963 | A1 | 7/2017 | Kondadadi | |

FOREIGN PATENT DOCUMENTS

| | | | |
|---|---|---|---|
| WO | 2016147079 | A1 | 9/2016 |

OTHER PUBLICATIONS

Bell et al. (JAMA Network Open (2020) vol. 3, No. 6:16 pages.*

International Search Report and Written Opinion of PCT/EP2019/056408, dated Jun. 26, 2019.

* cited by examiner

*Primary Examiner* — Lori A. Clow

(57) ABSTRACT

Systems for determining an erroneous code in a medical report comprising a plurality of codes, each code representing a comment in the medical report the system, comprise a memory comprising instruction data representing a set of instructions and a processor configured to communicate with the memory and to execute the set of instructions. The set of instructions, when executed by the processor, cause the processor to determine a respective vector representation for each of the plurality of codes in the medical report, wherein relative values of any selected pair of vector representations are correlated with a co-occurrence of the corresponding codes in a set of reference medical reports. The set of instructions when executed by the processor further cause the processor to determine an erroneous code in the medical report, based on the vector representations.

17 Claims, 4 Drawing Sheets

DETERMINING ERRONEOUS CODES IN MEDICAL REPORTS

This application is the U.S. National Phase application under 35 U.S.C. § 371 of International Application No. PCT/EP2019/056408, filed on Mar. 14, 2019, which claims the benefit of U.S. Provisional Application Ser. No. 62/642,958, filed Mar. 14, 2018. These applications are hereby incorporated by reference herein.

TECHNICAL FIELD

This disclosure relates to medical reports. More specifically, but non-exclusively, the disclosure relates to systems and methods for determining an erroneous code in a medical report.

BACKGROUND

The general background is in medical reporting. Medical reports may comprise free-text entries (e.g. clinical narratives) or structured medical reports. Structured medical reports use standardized and constrained language and may be constructed through selection of pre-defined codes (which may be called "finding codes", FCs) through a point-and-click process. Each code corresponds to an observation, diagnostic statement or other comment. For example, a code may correspond to the one sentence description "There is mild mitral regurgitation". One or more pre-defined codes may be selected and a final report construed by mapping the selected codes to their corresponding descriptions and positioning these sentences into a (structured) document.

Structured reporting has generally been shown to be more efficient in summarizing clinical findings and supporting downstream utilization such as quality improvement, clinical analytics and decision support. However, through human error, structured medical reports may contain contradictory codes (e.g. due to a medical practitioner accidentally selecting an inappropriate code). Such errors degrade the quality of reports and may confuse consumers (e.g. users) of the report. To improve quality control, plugins have been devised to provide error checking. For example, rule based checking has been employed to spot erroneous or conflicting codes in reports. One downside to the use of rule based systems is that they may require extensive rule sets comprising hundreds of manually configured rules. Furthermore, the codes themselves are usually configurable, and therefore hospitals and medical facilities may customise the codes used in their medical reporting, leading to different codes being used in different hospitals. As such, a different set of rules may be required to check medical reports in each medical facility. This is disadvantageous as the rules are created by skilled medical professionals and the process is time consuming and resource intensive. For such reasons, quality assurance tools based on such rule based approaches are not currently widely adopted.

SUMMARY

As described above, medical reports may be generated using predefined codes, where each code represents a comment in the medical report. Occasionally, due to for example, user error, conflicting or otherwise erroneous codes may be selected and such errors degrade the quality of medical reports and have a negative impact on user confidence in structured report generating systems. There is therefore a need for improved methods and systems that may determine erroneous codes in a medical report.

According to a first aspect there is provided a computer implemented method of determining an erroneous code in a medical report where the medical report comprises a plurality of codes, each code representing a comment in the medical report. The method comprises determining a respective vector representation for each of the plurality of codes in the medical report, wherein relative values of any selected pair of vector representations are correlated with a co-occurrence of the corresponding codes in a set of reference medical reports. The method further comprises determining an erroneous code in the medical report, based on the vector representations.

According to a second aspect there is provided a system for determining an erroneous code in a medical report, where the medical report comprises a plurality of codes, each code representing a comment in the medical report. The system comprises a memory comprising instruction data representing a set of instructions and a processor configured to communicate with the memory and to execute the set of instructions. The set of instructions, when executed by the processor, cause the processor to determine a respective vector representation for each of the plurality of codes in the medical report, wherein relative values of any selected pair of vector representations are correlated with a co-occurrence of the corresponding codes in a set of reference medical reports. The set of instructions, when executed by the processor, further cause the processor to determine an erroneous code in the medical report, based on the vector representations.

According to a third aspect there is provided a computer program product comprising a non-transitory computer readable medium, the computer readable medium having computer readable code embodied therein, the computer readable code being configured such that, on execution by a suitable computer or processor, the computer or processor is caused to perform the method of the first aspect.

In this way, erroneous codes may be determined in an automated process, without the input of a skilled medical professional. Furthermore, the method is transferable to any medical facility for which a set of reference medical reports is available. In this way, the methods and systems herein provide more efficient error checking of structured medical reports.

These and other aspects will be apparent from and elucidated with reference to the embodiments described hereinafter.

BRIEF DESCRIPTION OF THE DRAWINGS

For a better understanding of the embodiments, and to show more clearly how they may be carried into effect, reference will now be made, by way of example only, to the accompanying drawings, in which.

DETAILED DESCRIPTION OF EMBODIMENTS

As noted above, structured reporting can be used to generate standardised medical reports. Structured reporting lets a user select codes from a plurality of codes, each code representing a comment, to build up a medical report. Sometimes a user may select one or more erroneous codes, e.g. by mistake and this can undermine the accuracy of individual reports and the credibility of structured reporting as a method of generating reports. The systems and methods herein aim to improve this situation by enabling erroneous codes in a medical report to be quickly and accurately determined in an automated fashion without the need for supervision of a skilled medical professional.

Figure 1:
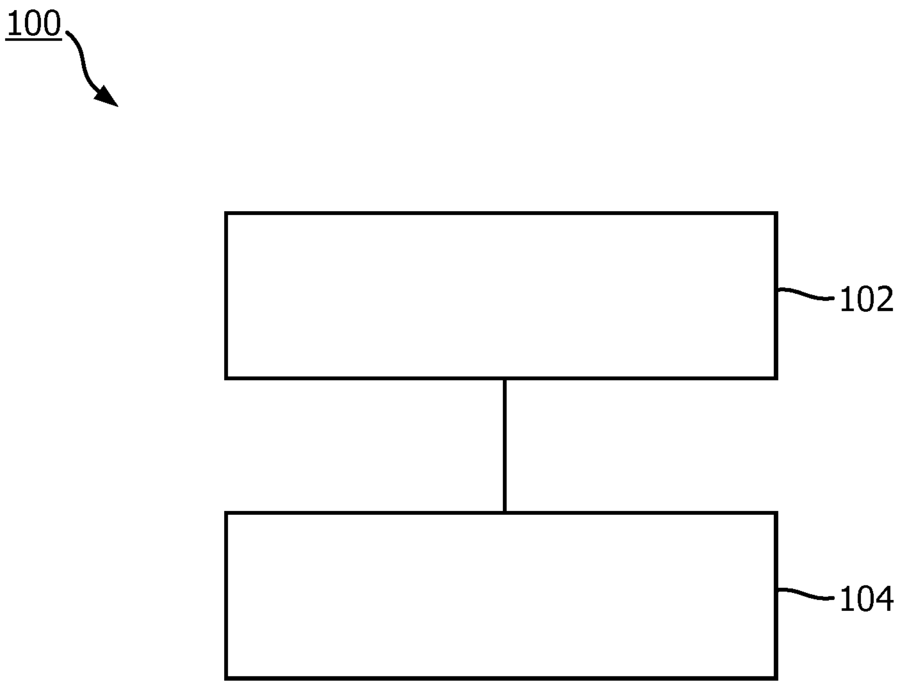
FIG. 1 is an example flowchart of an example method of determining an erroneous code in a medical report according to some embodiments herein.

FIG. 1 shows a computer implemented method of determining an erroneous code in a medical report according to some embodiments herein. The medical report comprises a plurality of codes, each code representing a comment in the medical report. In a first block 102 the method comprises determining a respective vector representation for each of the plurality of codes in the medical report, wherein relative values of any selected pair of vector representations are correlated with a co-occurrence of the corresponding codes in a set of reference medical reports. In a second block 104, the method comprises determining an erroneous code in the medical report, based on the vector representations.

As described above, the medical report may have been generated using structured reporting, whereby a user (e.g. medical professional) selects appropriate codes from a list or menu of possible codes. Each code is associated with a comment. A comment may comprise for example, words, numbers and/or sentences. Each comment may describe, for example, a clinical observation, a clinical statement, a clinical diagnosis or any other clinical information. The comments represented by the codes may be standardized. Examples of comments that may be represented by a code include, for example, "Diabetic", "High Blood Pressure", or "There is mild mitral regurgitation". In some scenarios, codes, as described herein may be referred to as "finding codes". Each medical report may comprise a plurality of such codes, which when taken together describe a clinical situation, clinical picture or clinical outcome.

In some embodiments, the block 102 may comprise determining a respective vector representation for each of the plurality of codes in the medical report. In this sense, each code in the medical report may be converted into vector form (e.g. the code may be converted into a sequence of numbers, each number representing a position (or co-ordinate) in a dimension of a hyper dimensional vector space).

The values of the vector components of each vector representation are determined with reference to their use or occurrence (e.g. relative to other codes) in a set of reference medical reports. The set of reference medical reports may comprise, for example, historical medical reports. The set of reference medical reports may comprise reports from an individual medical facility or hospital, or reports from a group of medical facilities or hospitals. Generally, the set of reference reports are generated using a common set of codes e.g. a common code base to the medical report. In some embodiments, the set of reference reports may, for example, comprise medical reports that have been checked to ensure that they do not contain erroneous codes and are therefore known to be accurate (e.g. the set of reference medical reports may have been checked by a medical professional).

Relative values of any selected pair of vector representations are correlated with a co-occurrence of the corresponding codes in the set of reference medical reports. Co-occurrence in this sense may mean the frequency with which the selected pair of codes appear in the same reports. Correlated in this sense may mean that the relative values of any selected pair of vector representations are related (e.g. proportional) to the co-occurrence of the pair of codes in the set of reference medical reports. Put another way, the relative values of any pair (e.g. any two) vector representations may be related to the frequency with which the selected pair of codes appear together in the set of reference reports.

For example, the vector representations of a first pair of codes may have more similar values (and thus be closer together in the aforementioned hyper dimensional vector space) than a second pair of codes, if the first pair of codes appear more frequently together in the same reports in the set of reference reports than the second pair of codes. The skilled person will appreciate however that this is merely an example, and the vector representations may be correlated with the co-occurrence of the codes in the set of reference medical reports in some other way.

In this way, the values of vector components of the vector representation of a code are determined with reference to the pattern in which that code occurs in the set of reference medical reports with respect to other codes in the set of reference medical reports. Because codes that appear more frequently together tend to relate to, for example, the same or similar medical conditions, or co-occurring illnesses or conditions, the values of the components of the vector representation for each code (e.g. the position of the code in the hyper dimensional space) thus reflects the clinical meaning or clinical context of the code. In this way, the method uses (clinical) semantics to convert the codes into vectors in the hyper dimensional space.

In some embodiments, the block 102 may comprise determining a respective vector representation for each of the plurality of codes using a machine learning process to determine each vector representation, based on a co-occurrence (e.g. co-occurrence patterns) of the corresponding codes in the set of reference medical reports. Using a machine learning process in this way avoids the need for manual review or laborious manual generation of quality assurance rules.

For example, the block 102 may comprise using a machine learning process that learns to represent each code as a vector e.g. according to its semantic meaning. The skilled person will be familiar with machine learning processes for converting words into vectors. For example, a shallow neural network may be trained to predict a missing word from a set of words (e.g. n-gram, or skipgram models including Word2Vec models such as continuous bag of words model, CBOW, models). A vector representation for a word may be determined from the values of weights of such a trained shallow neural network.

In this context, instead of converting words into vector representations, the inventors herein have recognised that similar machine learning processes may be used to convert codes in a medical report into vectors. For example, a neural network may be trained to predict a missing code from a series of codes in a medical report, based on the co-occurrence of such codes in the set of reference medical reports as described above. A vector representation for a word may be determined from the values of weights of a shallow neural network trained in this way. The skilled person will appreciate that this is only an example however, and that vector representations may be determined from the weights of a shallow neural network trained to perform other tasks related to the codes in the set of reference reports.

More generally, the skilled person will appreciate that other machine learning processes might be used to generate such vector representations, for example support vector machines or logistic regression models.

Generally, therefore, block 102 may comprise determining a respective vector representation for each code of the plurality of codes in the medical report, based on one or more weights or parameters of a machine learning model that has been trained to predict a code based on the occurrence (e.g. co-occurrence) of codes in the set of reference medical reports. In other words, a machine learning model trained to predict a code based on the pattern of use of the code, or linguistic context of the code in the set of reference medical texts.

Figure 2:
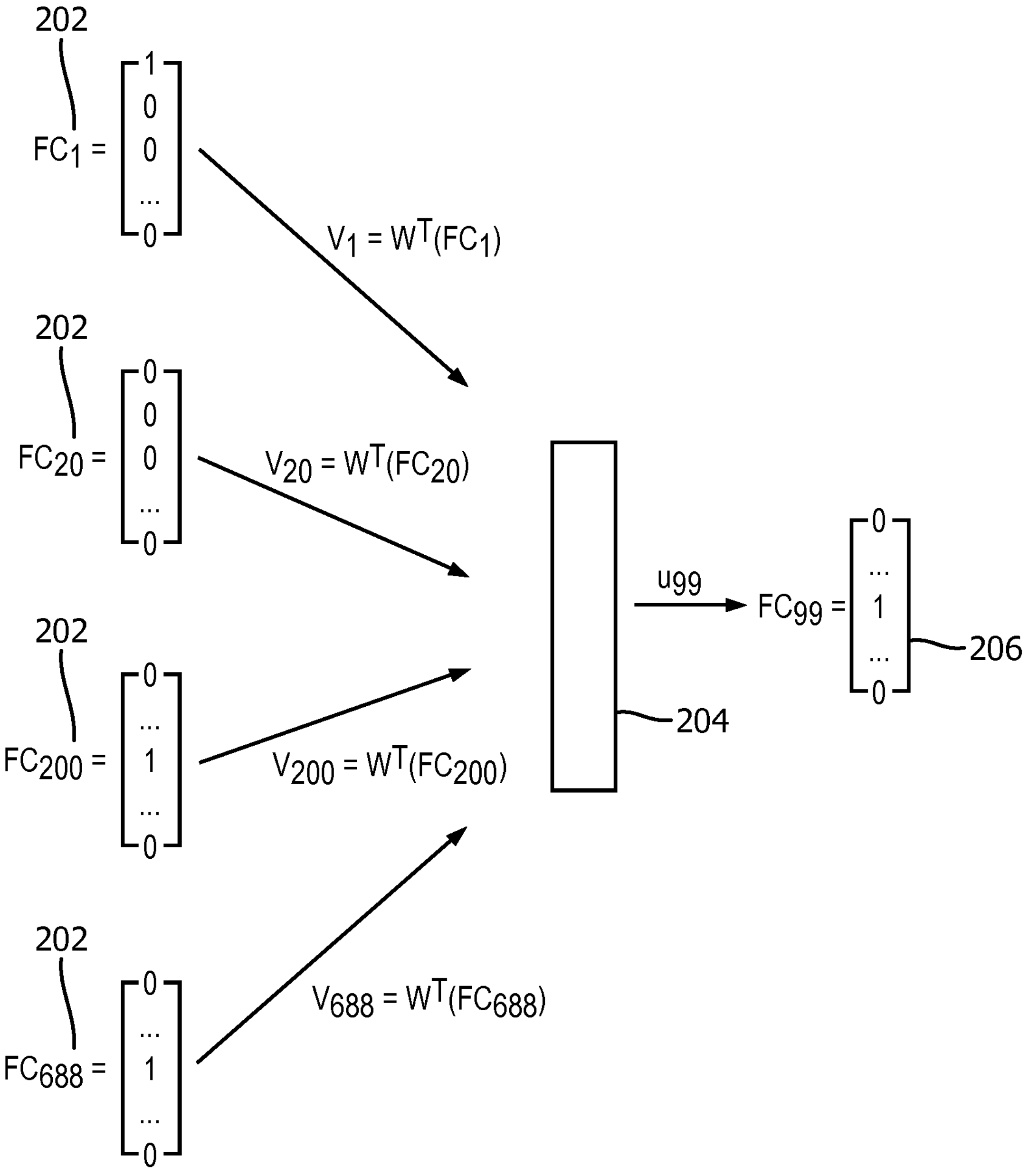
FIG. 2 illustrates an example method of determining a vector representation for a code.

This is illustrated in FIG. 2 which illustrates an example of how a machine learning model may be used to determine in block 102 a respective vector representation for each of the plurality of codes in a medical report according to some embodiments herein.

Given a set of reference medical reports (e.g. such as a database comprising structured reports), each report in the set of reference medical reports may comprise a plurality of codes 202. For example, a report may contain codes {"FC1", "FC20", "FC99", "FC200", "FC688"}. A machine learning model may be adapted to predict from a sequence of codes, another code that frequently occurs with, or appears in a similar context to the sequence of codes (e.g. a machine learning model may be used to predict what may be thought of as a "missing code"). Put another way, the machine learning model may treat {"FC1", "FC20", "FC200", "FC688"} as a context and from these codes, the model may predict another code (e.g. the "center" code) "FC99". As a by-product of this training process, the learning process of the machine learning model generates a numerical vectorised representation of each code. In this way a machine learning model may be used to determine a vector representation for each of the plurality of codes in a medical report that reflects how commonly this code occurs with respect to the other codes in each report (e.g. as described above, relative values of any selected pair of vector representations are correlated with a co-occurrence of the corresponding codes in the set of reference medical reports).

In more detail, each code may initially be represented as a V dimensional vector comprising 0s and one 1 at the index of that code in a list of possible codes. V is thus the size of (e.g. the number of codes in) the code list. The codes (labelled $FC_i$) may therefore be initially input to the machine learning model, for example, as:

$$FC_1 = \begin{bmatrix} 1 \\ 0 \\ 0 \\ \cdots \\ 0 \end{bmatrix}, FC_2 = \begin{bmatrix} 0 \\ 1 \\ 0 \\ \cdots \\ 0 \end{bmatrix}, \ldots , FC_v = \begin{bmatrix} 0 \\ 0 \\ 0 \\ \cdots \\ 1 \end{bmatrix}$$

A V×N dimensional parameter matrix W may then be defined, letting $v_i = W^T(FC_i)$ for each $FC_i$. An N dimensional vector $u_i$ may also be defined for each $FC_i$. In the machine learning model, $v_i$ is the result of transforming $FC_i$ in a linear model, $u_i$ is used as the weights to calculate a score to measure if the prediction is $FC_i$. Both W and $u_i$ are unknown parameters which may be learned by the machine learning algorithm. Turning back to FIG. 2, each code 202 in the pre-defined context/window size makes contributions to the hidden layer of the model. The output of the hidden layer is the average of vectors 204 corresponding to the input codes and this average code 204 can be used to predict a "missing" or similar code 206. Vector representations for each code can be determined from a model trained in this way (e.g. trained to predict missing or similar codes). For example, the learned vectors $v_i$ and $u_i$ for $FC_i$ can be concatenated and used as the vector representation for $FC_i$.

The initial list of codes may be specific to an individual or group of hospitals or medical institutions and may be generated using an automated process (e.g. via enumeration). In this way, the method above may be used to generate vector representations and thus determine erroneous codes in an automated manner, without the intervention of a skilled medical professional. The skilled person will appreciate however that this is merely an example and that vector representations may equivalently be determined from models trained for other tasks.

Generally speaking, and as described in the example with respect to FIG. 2, the vector representation for each code may therefore be determined based solely on the occurrence pattern of the codes themselves in the set of reference medical reports.

In other embodiments, the vector representations may be alternatively or additionally be determined based on other factors.

For example, in some embodiments, determining 102 a vector representation for each of the plurality of codes comprises, for each code: determining a plurality of word vector representations, the plurality of word vector representations comprising a vector representation for each word in the comment represented by the code, wherein relative values of any selected pair of vector representations in the plurality of word vector representations are correlated with a co-occurrence of the corresponding words in the set of reference medical reports. For example, each word in the comment represented by the code may be converted into a vector, based on the semantic context, e.g. how the words appear in the codes and how the codes appear in the set of reference documents.

Vectors for each word may be determined for the words comprised in the comments of the codes in the same manner as was described above, e.g. using a machine learning process such as n-gram, skip-gram, Word2Vec etc. If the longest comment represented by a code has L words, and each word can be represented as a 300-dimensional vector, each code comprises L×300 dimensional vector with zero paddings on empty spaces.

In some examples, the word vector representations may be determined (e.g. acquired) from a pre-trained or published word vectors database. For example, databases of pre-trained word vector representations containing up to 3 million words and phrases are currently available online. As these databases do not necessarily comprise medical terminology, there may exist new words in the codes that do not appear in such pre-trained databases. However, when the proportion of new words is low, for example, less than 10 percent, new words not found in the pre-trained database may be set to be zero vectors. If a higher percentage of words are not found in the pre-trained database, it may be more suitable to determine vector representations for the words in the comments by determining a new vector space and new vector representations, using the methods described above.

A vector representation for the code may be determined from the plurality of word vector representations, for example by combining the plurality of word vector representations into a single vector representation for the code. In some embodiments, the block 102 may comprise concatenating the plurality of word vector representations to obtain a concatenated word vector representation for the code. In some embodiments, the concatenated word vector representation may be used as the (overall) vector representation for the code.

In some embodiments, the approaches described above may be combined. For example, a vector representation for the code, determined as described above may be combined with the word vector representations for the words in the comment represented by the same code. This may produce a vector representation that is overall more consistent with the medical context of the code, as the more a word is consistent with a code's context, the more this word contributes to the final vector representation (e.g. the overall vector representation) for the code.

Therefore, in some embodiments, block 102 may additionally or alternatively further comprise for each code, combining (e.g. concatenating) the concatenated word vector representation with the vector representation for the code to create a combined vector representation for the code. Block 104 of determining an erroneous code in the medical report may then comprise determining an erroneous code in the medical report, based on the combined vector representations.

In this way, vector representations based solely on the pattern of use of the codes may be combined with vector representations for words in the comments represented by the codes.

In some embodiments, a vector representation for a code may be combined with the word vector representations for the words represented by the code using a weighted average. For example, the vector representation for the code may be used as a weight to weigh each word vector representation (for words in the comment represented by the code). The weighted word vector representations may then be averaged to produce a weighted average of the word vector representations.

As such, block 102 may additionally or alternatively further comprise for each code, weighting each vector representation in the plurality of word-vector representations using the vector representation for the code, and determining an average of the weighted word-vector representations to create an weighted-average vector representation for the code. The block of determining 104 an erroneous code in the medical report may then comprise determining an erroneous code in the medical report, based on the weighted average vector representations. In this way, the semantic meaning of the comments represented by the codes may be used to provide further insights into the pattern of use of the codes so as to leverage the insight that each code corresponds to a sentence. In this way, for example, it may be better determined that two codes that represent comments that are the same except for one keyword (e.g., "normal" versus "severe") have diametrically opposed meanings. This outcome may surface through analysis of the codes' associated comments, and may help enrich the semantic representation of the codes.

In some embodiments, block 102 may additionally or alternatively comprise, determining a vector representation for the code using a machine learning model which projects the two sources of vectors (e.g. a vector representation for the code and the word-vector representations for the words in the comment represented by the code) separately onto a new dimensional space, where each code then has one unique representation which may be used as the vector representation for the code.

Generally, it will be appreciated that in some embodiments, block 102 may comprise acquiring a vector representation for a code, for example from a database of codes. The vector representations in such a database may have been determined using any of the methods described herein.

Turning back to FIG. 1, in block 104, an erroneous code in the medical report is determined, based on the vector representations for the code. For example, determining an erroneous code may comprise determining an outlying vector representation. In this sense, an outlying vector representation may comprise, for example, a vector representation separated by more than a threshold separation from vector representations of other codes in the plurality of codes in a vector space. E.g. the vector representations of codes in the medical report may generally be clustered in a region of the vector space. Any code that is (e.g. statistically) outlying from such a cluster may be determined to be an outlying and possibly erroneous code in the report.

Generally, the cosine between any two vectors (or vector representations) is a measure of similarity: therefore the smaller the cosine between vector representations of two codes, the more semantically similar the corresponding two codes are. This perspective can be leveraged to run a decision logic that checks (e.g. in real time as a medical report is generated) whether a given code is an outlier compared to other codes in the medical report.

In some embodiments, an average separation of the vector representations in the vector space may be determined and outlying vector representations may be defined relative to the average separation. An average separation may be based, for example, on a predetermined number (or percentage) of the most separated vector representations in the vector space. This may ensure that a small number of highly correlated or tightly clustered codes do result in codes falsely being labelled as erroneous.

In some embodiments, a probability that each code comprises an outlying code may be determined for each code. For example, a probability may be determined based on a distance between different codes in the vector space. For example, a probability may be based on a normalised measure of separation of the plurality of codes in a vector space. For example, in some embodiments distances between codes may be mapped onto a scale representing whether a code is an outlier. For example, this scale may be the customary probability scale [0, 1]. E.g. the distances may be normalized relative to a central code in a cluster of codes in order to provide a probability that a code is an outlier relative to other codes in the cluster.

The skilled person will be familiar with other data mining techniques that may be used to determine outlying data points. For example, cosine similarities between vector representations of each code may be computed with respect to the other codes in the same report in a pairwise fashion. If a code is not close to any other codes, for example, within a predefined threshold, then this code may not fit the context of the medical report and may be determined or flagged as an outlier or erroneous code. In some embodiments a threshold may be set in order to determine a minimum distance of one code compared to all other codes in the report. Each code may be placed on a range from, for example, 0 to 1, where 0 indicates that the code is highly unlikely and 1 indicates that a code is highly likely to be an outlier.

It will be further appreciated that the method 100 may further comprise determining (or predicting) a missing code from the medical report, based on the vector representations. For example, code may be flagged as being missing from a medical report if that code is separated by less than a threshold separation from vector representations of other codes in the plurality of codes in a vector space. E.g. if the vector representation for the code is in the same cluster of vector representations as other codes in the medical report.

In this way, the method 100 may be used to determine erroneous and/or missing codes from a structured medical report comprising a plurality of codes. The computer implemented method 100 may be performed in real time, for example, as a user compiles a medical report, and as such, the user (such as a medical professional) may be provided with real-time feedback as to the accuracy of the medical report, to prevent erroneous codes from being used in the medical report.

Figure 3:
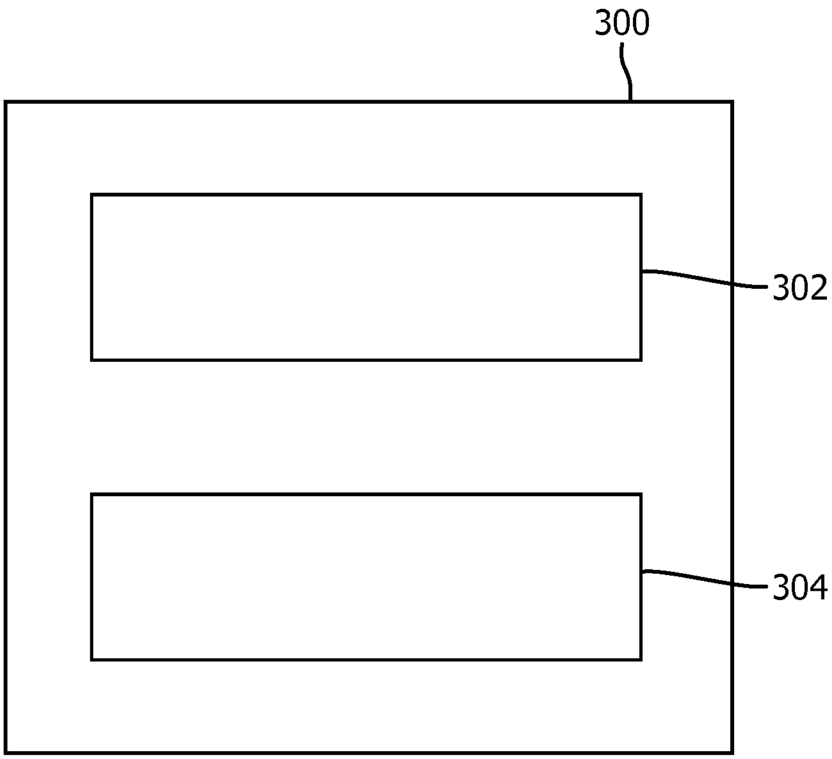
FIG. 3 is a schematic illustration of an example system for determining an erroneous code in a medical report according to some embodiments herein.

Turning now to FIG. 3, according to some embodiments, there is a system 300 for determining an erroneous code in a medical report according to some embodiments herein. The system 300 comprises a memory 304 comprising instruction data representing a set of instructions. The system 300 further comprises a processor 302 configured to communicate with the memory 304 and to execute the set of instructions. The set of instructions when executed by the processor may cause the processor to perform any of the embodiments of the method 100 as described above. The memory 304 may be configured to store the instruction data in the form of program code that can be executed by the processor 302 to perform the method 100 described above.

In some implementations, the instruction data can comprise a plurality of software and/or hardware modules that are each configured to perform, or are for performing, individual or multiple blocks of the method described herein. In some embodiments, the memory 304 may be part of a device that also comprises one or more other components of the system 300 (for example, the processor 302 and/or one or more other components of the system 300). In alternative embodiments, the memory 304 may be part of a separate device to the other components of the system 300.

In some embodiments, the memory 304 may comprise a plurality of sub-memories, each sub-memory being capable of storing a piece of instruction data. In some embodiments where the memory 304 comprises a plurality of sub-memories, instruction data representing the set of instructions may be stored at a single sub-memory. In other embodiments where the memory 304 comprises a plurality of sub-memories, instruction data representing the set of instructions may be stored at multiple sub-memories. Thus, according to some embodiments, the instruction data representing different instructions may be stored at one or more different locations in the system 300. In some embodiments, the memory 304 may be used to store information, such as the plurality of codes, the vector representations for each of the plurality of codes, or any other data relevant to calculations made by the processor 302 of the system 300 or from any other components of the system 300.

The processor 302 can comprise one or more processors, processing units, multi-core processors and/or modules that are configured or programmed to control the system 300 in the manner described herein. In some implementations, for example, the processor 302 may comprise a plurality of (for example, interoperated) processors, processing units, multi-core processors and/or modules configured for distributed processing. It will be appreciated by a person skilled in the art that such processors, processing units, multi-core processors and/or modules may be located in different locations and may perform different steps and/or different parts of a single step of the method described herein.

Briefly, the set of instructions, when executed by the processor 302, cause the processor 302 to determine a respective vector representation for each of the plurality of codes in the medical report, wherein relative values of any selected pair of vector representations are correlated with a co-occurrence of the corresponding codes in a set of reference medical reports. The set of instructions, when executed by the processor 302, further cause the processor 302 to determine an erroneous code in the medical report, based on the vector representations.

Determining a respective vector representation for each code in the plurality of codes and determining an erroneous code, were described in detail with respect to blocks 102 and 104 of the method 100 and the details therein will be understood to apply equally to the operation of the system 300.

It will be appreciated that the system 300 may comprise additional components to those illustrated in FIG. 3. For example, the system 300 may comprise one or more communication interfaces for example, for receiving the medical report, the set of reference medical reports, or any other information relevant to the method 100. The system 300 may further comprise one or more user interfaces such as a display screen, mouse, keyboard or any other user interface allowing information to be displayed to a user or input to be received from a user. In some embodiments, the system 300 may further comprise a power source such as a battery or mains power connection.

Figure 4:
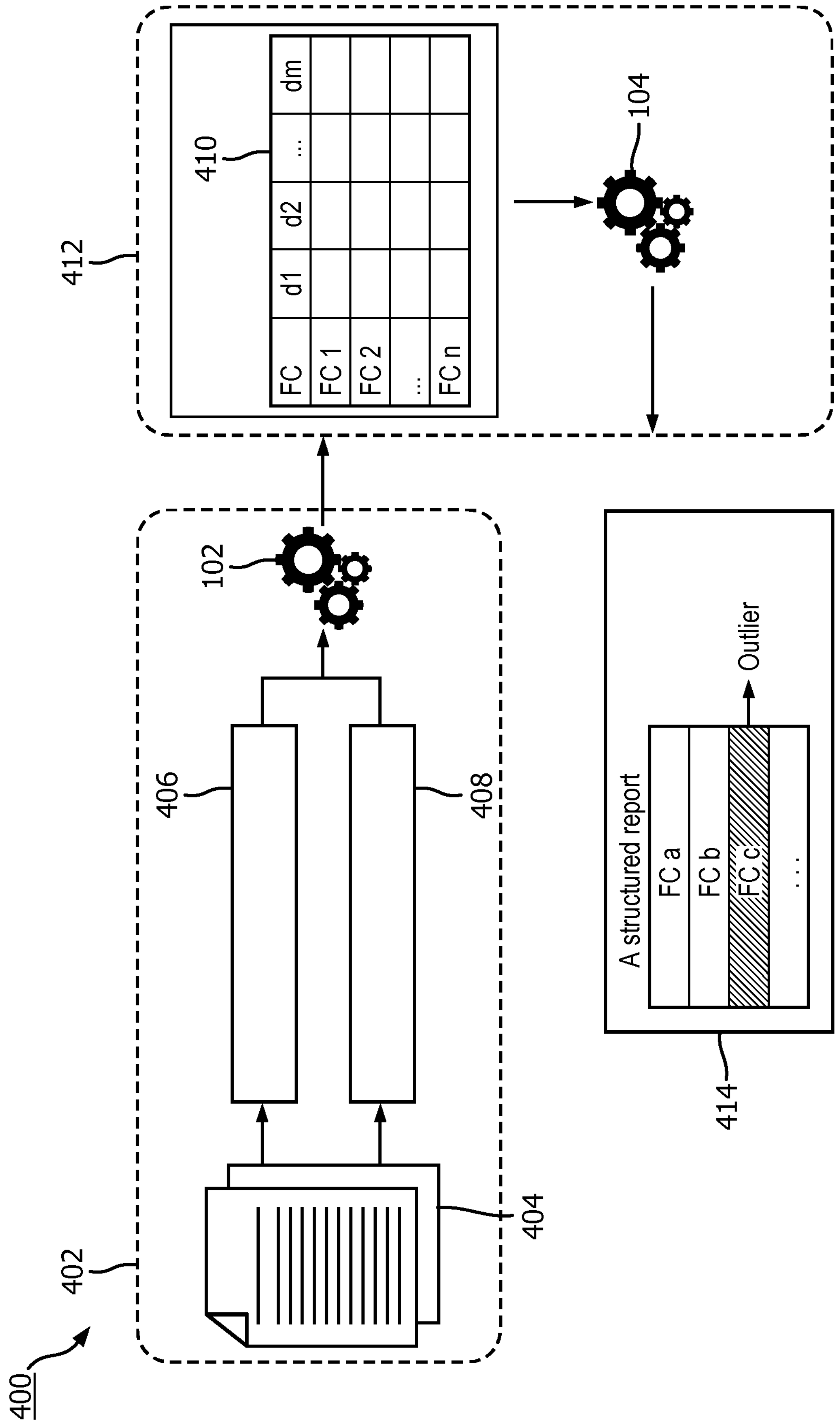
FIG. 4 is a schematic illustration of an example system for determining an erroneous code in a medical report according to some embodiments herein.

Turning now to FIG. 4, FIG. 4 illustrates a system 400 according to example embodiments herein. The system comprises a first module 402 that takes a set of reference medical reports 404 as input, determines (e.g. extracts) the codes 406 and comments 408 represented by the codes in each reference medical report in the set of reference medical reports 404 and, based on the set of reference medical reports, determines, as indicated by the symbol 102 in FIG. 4, a respective vector representation for each of the codes 406 in the set of reference medical reports. The relative values of any selected pair of determined vector representations are correlated with a co-occurrence of the corresponding codes in the set of reference medical reports, as described with respect to block 102 of method 100 above. Determining a respective vector representation for a code was described above with respect to block 102 of the method 100 and and the details therein will be understood to apply equally to the first module 402 of FIG. 4.

A list of vector representations 410 for the codes in the set of reference reports 404 is then sent to a second module 412 that determines, as indicated by the symbol 104 in FIG. 4, an erroneous code in a new (e.g. previously unseen) medical report, based on the vector representations 410. Determining an erroneous code in a medical report, based on vector representations was described above with respect to block 104 of method 100 and the details therein will be understood to apply equally to the second module 412 of FIG. 4.

The determined erroneous code(s) are then sent to a third module 414 which displays the determined erroneous code(s) to a user (for example, on a display screen of a computer, tablet or other computing device associated with the system 400). The codes in the (new) medical report may be ranked according to the likelihood that each code is an outlying code. The user may then re-evaluate the displayed erroneous code(s) and correct them as necessary.

It will be appreciated that any of the first 402, second 412 and/or third 414 modules may be comprised in, or may be separate from, associated structured report generation tools. The second 412 and third 414 modules may run in real time (e.g. as a medical report is generated) or in response to a user command, e.g. a user may trigger the second 412 and third 414 modules, for example, by uploading a medical report that is to be checked.

According to further embodiments, there is a computer program product comprising a non-transitory computer readable medium. The computer readable medium has computer readable code embodied therein. The computer readable code is configured such that, on execution by a suitable computer or processor, the computer or processor is caused to perform the method 100.

Because the systems and methods described herein can be trained and used in an unsupervised manner, no clinical domain knowledge is required to set the solution up on a new site. Thus the systems and methods described herein may be more efficient for skilled medical professionals to set up and use. In this way, the methods and systems herein may provide improved error reporting and quality control of structured medical reports.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method of determining an erroneous code in a medical report, comprising:

obtaining the medical report comprising a plurality of codes, each code representing a comment comprising clinical information;

generating a respective vector representation for each of the plurality of codes in the medical report, wherein values of a vector representation for a code of the plurality of codes are generated based on relation of the code in a set of reference medical reports to other codes in the set of reference medical reports, wherein relative values of a pair of vector representations are correlated with a co-occurrence of corresponding codes in the set of reference medical reports, wherein the respective vector representation is generated by converting the code into a plurality of position values that each represent a position in a dimension of a hyper dimensional vector space, each position value being determined to reflect a frequency that the code co-occurs with a respective one of the other codes in the set of reference medical reports and assigned to a vector component of the respective vector representation;

identifying at least one of the generated vector representations as an outlying vector representation relative to other vector representations for the plurality of codes in the medical report, wherein said identifying comprises determining that the at least one generated vector representations is separated by more than a threshold separation from the other vector representations based on the position values in the hyper dimensional vector space; and determining, based on the identification of the at least one generated vector representation as being an outlier and the position values in the hyper dimensional space, that the code represented by the at least one generated vector is an erroneous code in the medical report.

2. The method of claim 1, wherein determining a respective vector representation for each of the plurality of codes comprises:

for each code:

determining a plurality of word vector representations, the plurality of word vector representations comprising a vector representation for each word in the comment represented by the code, wherein relative values of any selected pair of vector representations in the plurality of word vector representations are correlated with a co-occurrence of the corresponding words in the set of reference medical reports.

3. The method of claim 2, further comprising, for each code:

concatenating the plurality of word vector representations to obtain a concatenated word vector representation for the code.

4. The method of claim 3, wherein the concatenated word vector representation is used as the vector representation for the code.

5. The method of claim 3, further comprising for each code:

concatenating the concatenated word vector representation with the vector representation for the code to create a combined vector representation for the code.

6. The method of claim 2, further comprising for each code:

weighting each vector representation in the plurality of word-vector representations using the vector representation for the code;

determining an average of the weighted word-vector representations to create a weighted-average vector representation for the code.

7. The method of claim 1, wherein determining a respective vector representation for each of the plurality of codes comprises:

using a machine learning process to determine each vector representation, based on a co-occurrence of the corresponding codes in the set of reference medical reports.

8. The method of claim 7, wherein the machine learning process comprises a Word2Vec process.

9. The method of claim 1, further comprising determining:

an average separation of the vector representations in a vector space; or an average separation of a predetermined number of a most separated vector representations in a vector space.

10. The method of claim 1, further comprising:

determining a probability that each code comprises an outlying code, based on a normalised measure of separation of the plurality of codes in a vector space.

11. The method of claim 1, further comprising predicting at least one additional code that could be missing from the medical report, based on the vector representations.

12. A non-transitory computer readable medium having stored instruction which, when executed by a processor, cause the processor to:

obtain a medical report comprising a plurality of codes, each code representing a comment comprising clinical information;

generate a respective vector representation for each of the plurality of codes in the medical report, wherein values of a vector representation for a code of the plurality of codes are generated based on relation of the code in a set of reference medical reports to other codes in the set of reference medical reports, wherein relative values of a pair of vector representations are correlated with a co-occurrence of corresponding codes in the set of reference medical reports, wherein the respective vector representation is generated by converting the code into a plurality of position values that each represent a position in a dimension of a hyper dimensional vector space, each position value determined to reflect a frequency that the code co-occurs with a respective one of the other codes in the set of reference medical reports and assigned to a vector component of the respective vector representation;

identify at least one of the generated vector representations as an outlying vector representation relative to other vector representations for the plurality of codes in the medical report, wherein said identifying comprises determining that the at least one generated vector representations is separated by more than a threshold separation from the other vector representations based on the position values in the hyper dimensional vector space; and determine, based on the identification of the at least one generated vector representation as being an outlier and the position values in the hyper dimensional space, that the code represented by the at least one generated vector is an erroneous code in the medical report.

13. A system for determining an erroneous code in a medical report;

the system comprising:

a memory comprising a set of instructions;

a processor configured to communicate with the memory and to execute the set of instructions, wherein the set of instructions, when executed by the processor, cause the processor to:

obtain a medical report comprising a plurality of codes, each code representing a comment comprising clinical information;

generate a respective vector representation for each of the plurality of codes in the medical report, wherein values of a vector representation for a code of the plurality of codes are generated based on relation of the code in a set of reference medical reports to other codes in the set of reference medical reports, wherein relative values of any pair of vector representations are correlated with a co-occurrence of corresponding codes of the pair of vector representations in the set of reference medical reports, wherein the respective vector representation is generated by converting the code into a plurality of position values that each represent a position in a dimension of a hyper dimensional vector space, each position value determined to reflect a frequency that the code co-occurs with a respective one of the other codes in the set of reference medical reports and assigned to a vector component of the respective vector representation;

identify at least one of the generated vector representations as an outlying vector representation relative to other vector representations for the plurality of codes in the medical report, wherein said identifying comprises determining that the at least one generated vector representations is separated by more than a threshold separation from the other vector representations based on the position values in the hyper dimensional vector space; and determine, based on the identification of the at least one generated vector representation as being an outlier and the position values in the hyper dimensional space, that the code represented by the at least one generated vector is an erroneous code in the medical report.

14. The system of claim 13, wherein the determination of a respective vector representation for each of the plurality of codes comprises, for each code:

determining a plurality of word vector representations, the plurality of word vector representations comprising a vector representation for each word in the comment represented by the code, wherein relative values of any selected pair of vector representations in the plurality of word vector representations are correlated with a co-occurrence of the corresponding words in the set of reference medical reports.

15. The system of claim 14, wherein the set of instructions, when executed by the processor, further causes the processor, for each code, to;

concatenate the plurality of word vector representations to obtain a concatenated word vector representation for the code, wherein the concatenated word vector representation is used as the vector representation for the code; and concatenate the concatenated word vector representation with the vector representation for the code to create a combined vector representation for the code.

16. The system of claim 14, wherein the set of instructions, when executed by the processor, further causes the processor, for each code, to weight each vector representation in the plurality of word-vector representations using the vector representation for the code, and determine an average of the weighted word-vector representations to create a weighted-average vector representation for the code.

17. The system of claim 13, wherein the set of instructions further causes the processor to determine an average separation of the vector representations in a vector space, or an average separation of a predetermined number of a most separated vector representations in a vector space.

* * * * *